(12) United States Patent
Van Acker et al.

(10) Patent No.: US 10,196,673 B2
(45) Date of Patent: Feb. 5, 2019

(54) ISOLATION OF NUCLEIC ACIDS

(71) Applicant: Biocartis N.V., Mechelen (BE)

(72) Inventors: Koen Van Acker, Mechelen (BE); Bart Claes, Mechelen (BE); Benoit Devogelaere, Vilvoorde (BE); Geert Maertens, Mechelen (BE); Erwin Sablon, Mechelen (BE); Pascale Holemans, Mechelen (BE); Tania Ivens, Mechelen (BE)

(73) Assignee: BIOCARTIS N.V., Mechelen (BE)

( * ) Notice: Subject to any disclaimer, the term of this patent is extended or adjusted under 35 U.S.C. 154(b) by 557 days.

(21) Appl. No.: 14/768,871

(22) PCT Filed: Feb. 18, 2014

(86) PCT No.: PCT/EP2014/053154
§ 371 (c)(1),
(2) Date: Aug. 19, 2015

(87) PCT Pub. No.: WO2014/128129
PCT Pub. Date: Aug. 28, 2014

(65) Prior Publication Data
US 2016/0002706 A1  Jan. 7, 2016

(30) Foreign Application Priority Data
Feb. 25, 2013  (EP) .................... 13156609

(51) Int. Cl.
*C12Q 1/68* (2018.01)
*C12Q 1/6806* (2018.01)
*C12Q 1/686* (2018.01)

(52) U.S. Cl.
CPC .......... *C12Q 1/6806* (2013.01); *C12Q 1/686* (2013.01)

(58) Field of Classification Search
CPC .................................. C12Q 1/6806
USPC ....................................... 435/6.1
See application file for complete search history.

(56) References Cited

U.S. PATENT DOCUMENTS

| | | | |
|---|---|---|---|
| 5,538,870 A | 7/1996 | Noeth et al. | |
| 6,469,159 B1 | 10/2002 | Belly et al. | |
| 2003/0134292 A1 | 7/2003 | Farchaus et al. | |
| 2011/0076751 A1 | 3/2011 | Fabis et al. | |
| 2011/0165610 A1 | 7/2011 | Baker et al. | |

FOREIGN PATENT DOCUMENTS

| EP | 1 904 234 B1 | 10/2011 |
|---|---|---|
| EP | 1 896 180 B1 | 11/2011 |
| JP | 1080279 A | 3/1998 |
| JP | 10506279 A | 6/1998 |
| JP | 2005523016 A | 8/2005 |
| JP | 2010535013 A | 11/2010 |
| JP | 2012-533296 A | 12/2012 |
| WO | 2010/118540 A1 | 10/2010 |
| WO | 2011/094577 A2 | 8/2011 |
| WO | 2011/008217 A1 | 11/2011 |
| WO | 2012/038462 A1 | 3/2012 |
| WO | 2012075133 A1 | 6/2012 |
| WO | 2013002354 A1 | 1/2013 |
| WO | 2013020089 A2 | 2/2013 |

OTHER PUBLICATIONS

International Search Report related to PCT/EP2014/053154 dated Apr. 15, 2014.
Slebos, Robert JC, et al. "A rapid and simple procedure for the routine detection of ras point mutations in formalin-fixed, paraffin-embedded tissues." Diagnostic Molecular Pathology 1.2 (1992): 136-141.
Andersen, F. Alan. "Final Report on the Safety Assessment of Oleth-2,-3,-4,-5,-6,-7,-8,-9,-10,-11,-12,-15,-16,-20,-23,-25,-30,-40,-44, and-501." International Journal of Toxicology 18.2 suppl (1999): 17-24.
Written Opinion corresponding to International Patent Application No. PCT/EP2014/053154, dated Apr. 15, 2014.
International Preliminary Report on Patentability corresponding to International Patent Application No. PCT/EP2014/053154, dated Aug. 25, 2015.
Chaw et al. (1980) "Isolation and identification of cross-links from formaldehyde-treated nucleic acids," Biochem. 19:5525-5531.
Easley et al. (2006) "A fully integrated microfluidic genetic analysis system with sample-in—answer-out capability," Proc. Natl. Acad. Sci. USA. 103(51):19272-19277.
Gilbert et al. (2007) "The isolation of nucleic acids from fixed, paraffin-embedded tissues-which methods are useful when?" PLoS One. 2(6):e537. pp. 1-12.
Goelz et al. (1985) "Purification of DNA from formaldehyde fixed and paraffin embedded human tissue," Biochem. Biophys. Res. Commun. 130(1):118-126.
Hamfjord et al. (2011) "Wobble-enhanced ARMS method for detection of KRAS and BRAF mutations," Diagn. Mol. Pathol. 20:158-165.
Metz et al. (2004) "Identification of formaldehyde-induced modifications in proteins: reactions with model peptides," J. Biol. Chem. 279:6235-6243.

*Primary Examiner* — Jezia Riley
(74) *Attorney, Agent, or Firm* — Lathrop Gage LLP; James H. Velema, Esq.

(57) ABSTRACT

Improved compositions for and methods of processing and analyzing samples are described. In particular, the compositions and methods liberate nucleic acids from a biological sample allowing direct downstream processing of the nucleic acids in microfluidic systems. These compositions, methods and kits are useful in diagnosing, staging or otherwise characterizing various biological conditions.

15 Claims, 7 Drawing Sheets

ISOLATION OF NUCLEIC ACIDS

RELATED APPLICATIONS

This application is a 35 U.S.C. § 371 filing of International Application No. PCT/EP2014/053154, filed Feb. 18, 2014, which claims priority to European Patent Application No. 13156609.3, filed Feb. 25, 2013, each of which is incorporated herein by reference in its entirety.

FIELD OF THE INVENTION

The present invention relates to improved compositions for and methods of processing and analysing samples. In particular, the invention relates to compositions, methods and kits for liberating nucleic acid from a biological sample allowing direct downstream processing of the nucleic acid. These compositions, methods and kits are useful in diagnosing, staging or otherwise characterizing various diseases.

BACKGROUND OF THE INVENTION

Microfluidic systems and combined microfluidic-microfluidic systems are attractive for diagnostics and allow for resource-limited settings because they use entire analytic protocols including sample pre-treatment, sample/reagent manipulation, separation, reaction, and detection integrated into a single platform. Current methods for lysing cells are based on mechanical lysis, thermal lysis, chemical lysis or electrical lysis. Once cells or samples have been lysed, or the nucleic acid is freed from the sample, microfluidic sensing systems require the nucleic acid to be purified or concentrated before delivery to a sensor. A wide range of nucleic acid extraction methods is available, each applying different types of chemistry and optimized for particular sample types. Because of their complex nature, most of the existing extraction methods are not appropriate for incorporation in microfluidic platforms or result in a significant loss of nucleic acids during the extraction step.

A variety of biological samples are taken from individuals to evaluate diagnostic and prognostic indicators of disease. Fresh tissue specimens, fixed and embedded samples and fine needle aspirate biopsies (FNA) are a valuable source of material for obtaining both molecular as well as clinical information since they often come from human specimens collected for examination of the histology of biopsies for the detection of disease. Tissue that is treated with a fixative, which prepares the sample for a variety of (immune-) histochemistry procedures, undergoes a variety of cross-linking modifications between nucleic acids and amino acids (Chaw Y. F. M. et al. Biochemistry 1980, 19: 5525-5531; Metz B. et al. J. Biol. Chem 2004. 279: 6235-6243). The fixed tissue is then encased in a block of embedding material (such as agar, gelatine or wax) which is hardened and cut into slices as little as 1-2 cell layers thick for histological studies. Compared to nucleic acid extraction from other sample sources, nucleic acid extraction from fixed and embedded sample slices requires the additional step of removal of the embedding material.

The use of formalin fixation and paraffin embedding (FFPE) to fix and preserve tissue samples is almost universal. A number of conventional protocols that solubilize paraffin and liberate nucleic acids from FFPE samples are available (Gilbert M. T. P. et al., PLoS One 2007, 2(6):e537). The traditional deparaffinisation methods start with a liquefaction step which uses an organic solvent, usually xylene, followed by a nucleic acid extraction step (Goezl et al., Biochemical and Biophysical Research Communication 1985, Vol. 130 No. 1, p 118-126). Xylene has the major disadvantages of being flammable, volatile, toxic and incompatible with plastic, making it less suitable for use in automated systems.

Nucleic acid preparation from tissue slice samples typically requires a proteinase step, most often incubation with a heat-stable protease in the presence of surfactants, to release the nucleic acid and degrade inhibitors that can interfere with downstream nucleic acid analysis. The amount of nucleic acid released is oftentimes minute because very little actual tissue is present in the slice and, in the case of an FFPE tissue slice, nucleic acids are frequently degraded. As a consequence, in the conventional methods, the nucleic acid most often needs to be concentrated before delivery to a downstream sensor in automated systems.

Non-toxic solutions for deparaffinization have been explored and improvements on nucleic acid recovery methods applicable on FFPE samples have been made available at the lab-scale level (e.g. WAXFREE™ Kit from Trimgen, ExpressArt FFPE Clear RNAready Kit from Amplification Technologies, BiOstic™ FFPE Tissue Isolation Kit from Mo Bio Laboratories, and QuickExtract™ FFPE DNA Extraction Kit from Epicentre).

One such improvement is described in WO2012/075133 and provides methods for in situ nucleic acid isolation from samples embedded in a hydrophobic matrix such as paraffin or a paraffin-blend. An emulsified lysate is hereto generated in the presence of a thermostable protease, and an additive selected from alkylene glycol, a poly-alkylene glycerol, or a block copolymer having an average molecular weight of 76 to 2900 Da, or a salt. Different additives are used for emulsifying the sample, including PEG200, PEG400, PEG1000, Brij30, Brij35P, Brij56 and Brij 76. The emulsified lysate is obtained in the presence of a mild chaotrope (e.g. urea or formamide) and heating. The method eliminates the need of physical separation of paraffin and the use of organic solvents such as xylene in a deparaffinization step. However, subsequent extraction of the nucleic acids from the emulsified lysate remains required for further downstream applications such as e.g. nucleic acid quantification by polymerase chain reaction, and such method might not be compatible with microfluidic systems Integrating a nucleic acid extraction protocol into a microfluidic platform requires a great effort to optimize yield and minimize nucleic acid loss. Furthermore, extraction is also a time-consuming step in the sample preparation procedure. In addition, extraction introduces a size bias (loss of smaller fragments) in the eluted nucleic acids, which is especially problematic when isolating nucleic acids from FFPE samples, which contain degraded nucleic acids. Therefore, a method that is uniformly applicable for obtaining nucleic acids from a broad range of biological samples, including FFPE samples in a condition allowing automated microfluidic system processing and direct downstream analysis would provide a great advantage compared to existing methods. In particular, FFPE samples in a condition allowing automated microfluidic system processing and direct downstream analysis, without the risk of losing certain nucleic acid fragments and introducing a length and purity bias, would provide a great advantage compared to existing methods.

There is thus a need to improve the sample preparation process allowing automated high throughput processing and detection of nucleic acid in various biological samples.

SUMMARY OF THE INVENTION

The present invention provides for nucleic acids liberated from biological samples in an environment that interfaces with downstream applications such as amplification processes. Compositions and methods described herein eliminate the requirement of separate nucleic acid extraction steps prior to downstream nucleic acid analysis. The sample preparation processes and compositions enable automated processing and are particularly suitable for implementation into microfluidic nucleic acid diagnostic systems. The present invention overcomes shortcomings of the conventional art and may achieve other advantages not contemplated by the conventional processes.

In particular, the present invention provides for nucleic acids liberated from biological samples in an environment that interfaces with downstream applications such as amplification processes within a microfluidic system. Compositions and methods described herein eliminate the requirement of separate nucleic acid extraction steps and eliminate the need for nucleic acid extraction steps, reduce potential bias and eliminate the need for diluting the liberated nucleic acids prior to downstream nucleic acid analysis.

In general terms, it is an aspect of the invention to provide a method for releasing nucleic acid from a biological sample enabling direct nucleic acid analysis in a microfluidic system comprising the step of
  contacting the sample with a composition under conditions to provide a lysate compatible with downstream nucleic acid analysis systems.

In particularly, it is an aspect of the invention to provide a method for releasing nucleic acids from a biological sample enabling direct nucleic acid analysis in a microfluidic system comprising the steps of
  contacting the sample with a composition under conditions to provide a lysate compatible with downstream nucleic acid analysis systems, and
  analysing the nucleic acid directly in the lysate.

More particularly, it is an aspect of the invention to provide a method for releasing nucleic acid from a biological sample enabling direct nucleic acid analysis in a microfluidic system comprising the steps of
  contacting the sample with a composition under conditions to provide a lysate compatible with downstream nucleic acid analysis systems,
  processing the lysate in a microfluidic system for nucleic acid analysis, and
  analysing the nucleic acid directly in the lysate.

More particularly, it is an aspect of the invention to provide a method for releasing nucleic acids from a biological sample enabling direct nucleic acid analysis in a microfluidic system comprising the steps of
  contacting the sample with a composition under conditions to provide a lysate compatible with downstream nucleic acid analysis systems, and
  analysing the nucleic acid directly in the undiluted or minimally diluted lysate within the microfluidic system.

More particularly, it is an aspect of the invention to provide a method for releasing nucleic acid from a biological sample enabling direct nucleic acid analysis in a microfluidic system comprising the steps of
  contacting the sample with a composition under conditions to provide a lysate compatible with downstream nucleic acid analysis systems,
  processing the lysate in a microfluidic system for nucleic acid analysis, and
  analysing the nucleic acid directly in the undiluted or minimally diluted lysate within the microfluidic system.

In particular, it is an aspect of the invention to provide a method for releasing nucleic acids contained in a biological sample, the method comprising the step of:
  contacting the biological sample with a composition for converting at least part of the sample into a lysate containing said nucleic acids, said lysate being directly transportable through a microfluidic system;
  analysing the nucleic acid contained in the lysate within the microfluidic system.

More in particular, it is an aspect of the invention to provide a method for releasing nucleic acids contained in a biological sample, the method comprising the step of:
  contacting the biological sample with a composition for converting at least part of the sample into a lysate containing said nucleic acids, said lysate being directly transportable through a microfluidic system;
  analysing the nucleic acid directly in the lysate within the microfluidic system.

Methods of the invention include combinations of inventive methods and compositions working together to enhance the sensitivity and accuracy of nucleic acid determination.

It is thus also an aspect of the present invention to provide a method for analysing nucleic acid released from a biological sample in a microfluidic system, which method incorporates the steps of:
  contacting the sample with a composition under conditions to provide a lysate compatible with downstream nucleic acid analysis systems, and
  analyzing the nucleic acid directly in the lysate.

Preferably, in all aspects, the nucleic acid is analysed directly in the lysate within the microfluidic system.

It is a further aspect of the present invention to provide a method for analysing nucleic acid released from a biological sample in a microfluidic system, which method incorporates the steps of:
  contacting the sample with a composition under conditions to provide a lysate compatible with downstream nucleic acid analysis systems,
  processing the lysate in a microfluidic system for direct nucleic acid analysis, and
  analyzing the nucleic acid directly in the lysate In particular embodiments, the methods of the present invention are applicable on fresh tissue samples and/or fresh frozen tissue samples and/or fixed tissue samples and/or embedded tissue samples. In particular embodiments, the biological sample is a biopsy sample, a fixed sample, a wax-embedded sample and/or a FFPE sample.

In particular embodiments, the composition for use in the methods of the invention has liquefying properties. In preferred embodiments, the method is applicable for liquefying and/or dissolving wax from a wax containing biological sample.

In particular embodiments, the composition for use in the methods of the present invention had properties similar to the essential properties of the composition presently described.

Thus, in another aspect of the invention, compositions for releasing nucleic acid from a biological sample enabling direct nucleic acid analysis in a microfluidic system are provided, which compositions comprises a surfactant compatible with downstream nucleic acid analysis systems. Preferably, compositions for releasing nucleic acid from a biological sample to form a lysate enabling nucleic acid analysis directly in the lysate within a microfluidic system are provided, which compositions comprises a surfactant compatible with downstream nucleic acid analysis systems. Preferably, the composition when contacted with a sample will provide a lysate, which lysate in its undiluted form is compatible with downstream nucleic acid analysis systems. Preferably, the lysate in its undiluted form or minor diluted form is compatible with downstream nucleic acid analysis systems. In preferred embodiments, the compositions have emulsifying properties and comprise a non-ionic surfactant compatible with downstream nucleic acid analysis. Preferably, the non-ionic surfactant has the formula R—O—$(CH_2CH_2O)_n$H wherein n>7, n≥8, or n=8; R comprises 12≤C≤38, R is an alkyl chain, R is $CH_3(CH_2)_7$—CH=CH—$(CH_2)_8$, or R is $(CH_2)_{11}(CH_3)$. Preferably, the non-ionic surfactant is a C13(iso-tridecyl) fatty alcohol PEG ether or an oleyl alcohol PEG ether. Most preferably the surfactant is Oleth®-8. Oleth®-8 corresponds to (Z)-3,6,9,12,15,18,21,24-Octaoxadotetracont-33-en-1-ol (CAS number 27040-03-5).

In certain embodiments, the compositions include at least a non-ionic surfactant, a thermo stable protease and a pH-buffering agent and are particularly useful to generate an emulsified lysate when brought in contact under heating with a wax containing sample, which emulsified lysate in its undiluted form is compatible with and can be processed directly by microfluidic systems for nucleic acid analyses. Preferably, the emulsified lysate in its undiluted form or minor diluted form is compatible with and can be processed directly by microfluidic systems for nucleic acid analyses.

It is a further aspect of the present invention to provide a kit for obtaining a nucleic acid from a sample that can be processed directly by a microfluidic analyzer, which kit comprises at least a composition of the present invention.

These and further features of the present invention will become more apparent from the claims and detailed description provided herein.

DETAILED DESCRIPTION OF THE INVENTION

Figure 1:
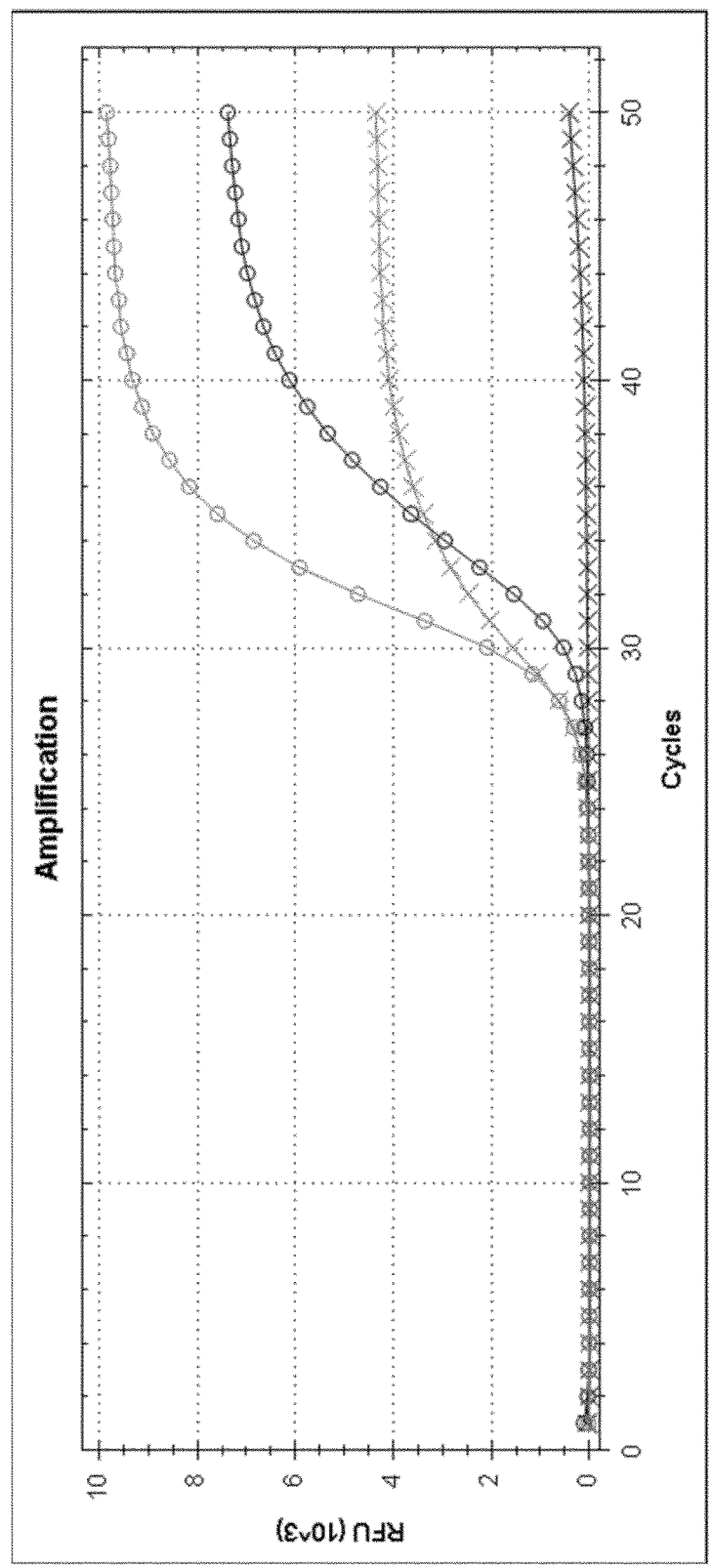
FIG. 1: Graph depicting PCR compatibility of the liquefied lysate obtained from FFPE tissue samples using two different methods. X-axis represents the number of amplification cycles; Y-axis represents relative fluorescence units (RFU) (103). Amplification curves representing the liquefaction composition containing the detergent Oleth®-8 (grey) and the commercial liquefaction buffer (black) are shown; cross-marked curves represent almost undiluted samples, circle-marked curves represent 4-fold diluted samples. The minor diluted samples represent 80/20 ratio of lysate/PCR amplification mix.

Techniques for nucleic acid extraction from biological tissue samples commonly use two separate steps: a/ digestion of the tissue followed by b/ purification of the nucleic acids. Techniques for nucleic acid extraction from wax containing samples commonly use three separate steps: a/ de-waxing; followed by b/ digestion of the tissue; and c/ purification of the nucleic acids. Overall, these methods are most frequently time consuming and/or not directly transferrable into fully integrated diagnostic systems most often because the nucleic acid extraction requires complicating reagents (e.g. ethanol) and substeps such as centrifugation of the sample, or incompatibility with plastics (xylene) or fluidics (for example due to foam formation in the channels). Methods and compositions provided herein allow now for the direct analysis of nucleic acids from biological samples, including wax containing samples, without requiring prior purification of the nucleic acid from the sample.

The invention hereto provides compositions for releasing nucleic acids from various biological samples, including wax containing samples. The compositions find their application in methods for releasing nucleic acid from a sample enabling direct nucleic acid analysis in a microfluidic system, and in methods for analysing the nucleic acid released from a sample in a microfluidic system. In particular applications, the methods comprise the step of contacting a biological sample with a composition under conditions to provide a lysate allowing the release of nucleic acid from the sample, which lysate is compatible with microfluidic systems designed for downstream nucleic acid analysis. The lysate is a liquid sample and may be a simple lysate, or alternatively may be the result from an incubation with an enzyme, such as a protease. In this application the use of "lysate" means "lysate", "liquid sample" or "digest" unless stated otherwise. The lysate is ready for direct nucleic acid analysis without requiring further purification of the released nucleic acid from the lysate. The nucleic acid can be analysed directly in the lysate.

Direct nucleic acid analysis refers to an analysis of nucleic acid released in a lysate without requiring purification of the nucleic acid from detergents, proteins, salts and reagents used during the lysis step. The method is uniformly applicable for obtaining nucleic acids from a broad range of biological samples in a condition allowing automated microfluidic system processing and direct downstream analysis without the risk of losing certain nucleic acid fragments and introducing a length and purity bias. For instance no ethanol precipitation, phenol-chloroform extraction or mini-column purification is required. It is expected that the genetic information is representative when no purification steps are used. The nucleic acid analysis, in particular the nucleic acid amplification, may in some instances require a minor diluted form of the lysate for reasons of e.g. diluting potent inhibitors of the amplification enzymes, diluting substances that destabilize the enzymes, . . . . The nucleic acid analysis, in particular the nucleic acid amplification, may or may not require the addition of substances for performing an amplification of the nucleic acid, and accordingly may result in a minor dilution of the initial lysate. The substances required for further downstream processing of the sample may be provided in a dried format and may be dissolved directly in the lysate.

Minor diluted form refers to diluting the nucleic acid lysate with nucleic acid lysate amplification substances anywhere in the range of undiluted to a 2-fold dilution.

Accordingly, the invention provides for a method for releasing nucleic acid from a biological sample enabling direct nucleic acid analysis in a microfluidic system comprising the steps of
  contacting the sample with a composition under conditions to provide a lysate compatible with downstream nucleic acid analysis systems,
  processing the lysate in a microfluidic system for nucleic acid analysis, and
  analyzing the nucleic acid directly in the lysate.

Particularly, the invention provides for a method for releasing nucleic acids contained in a biological sample, the method comprising the step of:
  contacting the biological sample with a composition for converting at least part of the sample into a lysate containing said nucleic acids, said lysate being directly transportable through a microfluidic system;
  analyzing the nucleic acid contained in the lysate within the microfluidic system.

In particular, the invention provides for a method for releasing nucleic acids contained in a biological sample, the method comprising the step of:
  contacting the biological sample with a composition for converting at least part of the sample into a lysate containing said nucleic acids, said lysate being directly transportable through a microfluidic system;
  analyzing the nucleic acid directly in the lysate within the microfluidic system.

Accordingly, the invention provides for a method for analysing nucleic acid released from a biological sample in a microfluidic system, which method incorporates the steps of:
  contacting the sample with a composition under conditions to provide a lysate compatible with downstream nucleic acid analysis systems,
  processing the lysate in a microfluidic system for direct nucleic acid analysis, and
  analyzing the nucleic acid directly in the lysate.

More in particular, the invention provides for a method for analysing nucleic acid released from a biological sample in a microfluidic system, which method incorporates the steps of:
  in the microfluidic system, contacting the sample with a composition under conditions to provide a lysate compatible with downstream nucleic acid analysis systems,
  processing the lysate in said microfluidic system for direct nucleic acid analysis, and
  analyzing the nucleic acid directly in the lysate "Nucleic acid" (and the equivalent term "polynucleotide") as used herein, refers to a polymer of ribonucleosides or deoxyribonucleosides comprising phosphodiester linkages between nucleotide subunits. Nucleic acids include, but are not limited to, genomic DNA, cDNA, hnRNA, mRNA, rRNA, tRNA, microRNA, fragmented nucleic acid, nucleic acid obtained from subcellular organelles such as mitochondria, and nucleic acid obtained from microorganisms or viruses that may be present on or in a sample. The nucleic acid can be double-stranded or single-stranded, circular or linear. Preferably the nucleic acid is released from a biological sample. The nucleic acid is composed of DNA and RNA, and he RNA is preferably total RNA. "Sample or biological sample" is intended to include a variety of biological sources that contain nucleic acid and/or cellular material. The nucleic acid and/or cellular material are from cells being tested to determine whether one or more particular markers are present. Samples included are samples from cultures of cells, eukaryotic microorganisms or diagnostic samples such as a body fluid, body fluid precipitate, lavage specimen, fine needle aspirate, biopsy sample, tissue sample, cancer cells, cells from a patient, cells from a tissue or in vitro cultured cells from an individual being tested and/or treated for disease or infection, or forensic samples. Non-limited examples of body fluid samples include whole blood, bone marrow, cerebral spinal fluid, peritoneal fluid, pleural fluid, lymph fluid, serum, plasma, urine, chyle, stool, ejaculate, sputum, nipple aspirate, saliva, swabs specimen, wash or lavage fluid and/or brush specimens.

In certain embodiments, the sample is a fresh sample, a fresh frozen sample, a fine needle aspirate, a sample that has been treated for preservation and may contain cross-linking of reactive sites due to fixation treatment, a wax-contacted or wax-embedded sample, or an FFPE sample in the form of an FFPE slice. Fresh-frozen samples are samples which have been hardened and embedded in a cryo-solidifiable medium, such as a OCT-compound. Fine needle aspirates as used herein include but are not limited to cells that following centrifugation have been wax-embedded, with or without prior fixation treatment.

"Wax" refers to a composition used in the histochemical art for embedding biological samples for histochemical or other analyses, usually consisting of a complex mixture of higher hydrocarbons often including esters or higher fatty acids and higher glycols, and may be mineral, natural or synthetic in origin.

Paraffin is an example of a wax most commonly used in the histochemical field. The term "paraffin" is used synonymously with "alkane", indicating hydrocarbons with the general formula $C_nH_{2n+2}$. As used herein, the term "paraffin" includes paraffin wax and paraffin blend type embedding media. "Paraffin wax" refers to a mixture of alkanes that falls within the $20 \leq n \leq 40$ range. Paraffin blends include further materials that may enhance properties of the paraffin in embedding procedures.

Chemical fixatives preserve tissue from degradation and assist in maintaining the structure of cells and sub-cellular components. Embedded biological samples generally are preserved or archived in the form of formalin-fixed paraffin-embedded samples (FFPE samples). "FFPE" refers to tissues or cells that have been treated by exposure to neutral buffered formalin (usually 4% formaldehyde in phosphate buffered saline) and subsequently soaked thoroughly in a hydrophobic matrix such as paraffin or a paraffin blend so that the paraffin or the paraffin blend has infiltrated the tissues or cells.

As a non-limiting example shown in the example section, the methods of the invention are successfully practiced on melanoma samples. Thus, in certain embodiments of the invention, the sample is a biological sample from an individual being interrogated for a biological state such as a health condition, a disease or an infection. Alternatively, the sample is from an individual diagnosed for a biological state but interrogated for prognosis or therapeutic intervention such as treatment selection or treatment outcome. In particular embodiments the biological state is a disease and involves a neoplasia disorder, in particular a tumor or a cancer.

A biological state, disease, infection or a response to therapeutic intervention can be assessed with use of markers.

"Marker", "test marker", "biomarker" or "biological marker" is a characteristic that is objectively measured an evaluated and refers to a cellular component specific to a particular biological state. The marker may be a nucleic acid or a protein component or parts thereof. Preferably, it is a nucleic acid, DNA or RNA.

In one embodiment, markers are intended to include but are not limited to, translocations, microsatellites, alleles, mutations, single nucleotide polymorphisms (SNPs), insertions, deletions, splice variants, transposons, microRNA's, expression profiles, etc. associated with a disease or infection. In some embodiments, DNA is used to identify SNPs, insertions, deletions or translocations. In other embodiments, RNA is used to identify expression levels. Expression levels can eventually be linked to SNPs or other genetic variations. The example section shows that the methods of the invention were successfully used for detecting the presence of the BRAF gene. Specific assays exist to detect the presence of mutated variants of this gene (e.g. based on Hamfjord et al., Diagn Mol Pathol 2011; 20:158-165). Accordingly, in certain embodiments, the markers are markers applicable for diagnosis or prognosis of cancer or disease, for the prediction of cancer or disease treatment outcome, for the selection of patients suitable for treatment, for the selection of the treatment regimens to be used, or for selecting treatment regimen change. In certain embodiments, the markers include nucleic acid modifications associated with a disease, preferably mutations, SNPs, insertions, deletions or translocations.

In the methods of the present invention, a sample is contacted with a composition to provide a lysate in which nucleic acid is released, which composition is optimized for use in microfluidic analysers. The composition is transportable through a microfluidic system. In certain embodiments of the supplied methods, such contacting step may thus be implemented in the microfluidic system itself or alternatively may require manual pipetting by a researcher prior to microfluidic system analysis. Thus, in certain embodiments, the microfluidic system may accept the sample and process the sample using the methods of the invention prior to analysis. In certain embodiments, the system will accept and analyse the lysate prepared beforehand.

By "contacting" is meant coming together, exposing, incubating, or mixing of the sample and the composition.

Methods of the invention include combinations of inventive physical (heat, HiFu, . . . ) and biochemical (enzymes, salts, reducing agents, . . . ) methods and compositions working together to enhance the sensitivity and accuracy of nucleic acid determination. As shown in the example section, subjecting the composition to heating and HIFU gives improved emulsifying capacity compared to a composition subjected to heating in combination with stirring or shaking. In particular, heating temperatures to around 60° C. (e.g. 60° C.±1° C.; 60° C.±2° C., 60° C.±3° C., 60° C.±4° C., 60° C.±5° C.) gives an improved emulsifying effect. In preferred embodiments, the temperature is raised stepwise from room temperature to 60° C., followed by HIFU treatment. Preferably, the HIFU power does not exceed 2.25 W.

"Releasing" refers to liberating, obtaining and/or reversal of cross-linking. For liberating nucleic acid from a sample, protease activity and pH-buffering may be required from the composition. Releasing may require from the composition potential precipitating activity of components other than nucleic acid present in the investigated sample and removal/dissolving of fixative. Releasing may require conditions such as heating or High-Intensity Focused Ultrasound (HIFU). Nucleic acid obtained from FFPE samples typically contains nucleotide-to-nucleotide and nucleotide-to-protein cross-links, base modifications and other chemical modifications that affect the integrity of the nucleic acid.

In one embodiment, the lysate and/or components released from the sample will be processed in microfabricated diagnostic analysers using microfluidic systems. "Microfluidic system" refers to systems dealing with the behaviour, precise control and manipulation of fluids that are geometrically constrained to a small, typically sub-millimeter, scale. Small volume fluids are moved, mixed, separated or otherwise processed at micro scale requiring small size and low energy consumption. Microfluidic systems include structures such as micro pneumatic systems, i.e. microsystems for the handling of off-chip fluids (pressure sources, liquid pumps, micro valves, etc. . . . ) and microfluidic structures for the on-chip handling of micro, nano- and picoliter volumes (microfluidic channels, etc. . . . ). Microfluidic systems aim to integrate assay operations such as detection, as well as sample pre-treatment and sample preparation on one system. Devices and methods for conducting microfluidic analysis may incorporate biochips based on a DNA microarray or protein microarray, and/or devices for conducting thermo cycling (e.g. PCR, LCR, and others) and/or devices for sequencing. In certain embodiments of the present invention, the microfluidic system will incorporate microfabricated analysis systems, requiring manipulation of the sample and liquefaction buffer outside the system. In preferred embodiments, the microfluidic system will integrate the steps for providing a lysate as described in the methods of present invention, and be a fully integrated system that completes an assay from sample-in to result-out. In terms of nucleic acid analysis, the microfluidic system may thus be an integrated microsystem simultaneously implementing nucleic acid preparation and release as well as marker analysis including target amplification and detection. Particularly, the method of the present invention comprises the steps of: contacting the biological sample with a composition for converting at least part of the sample into a lysate containing said nucleic acids within a microfluidic system, said lysate being directly transportable through the microfluidic system and analyzing the nucleic acid directly in the lysate within the microfluidic system. Accordingly, the lysate produced according to the methods of the invention should thus be directly transportable through a microfluidic system.

Suitable microsystems have been described in EP1896180, EP1904234 and EP2419705 and are accordingly incorporated in certain embodiments describing the present invention. Preferably, cartridge-based systems containing one or more reaction chambers and one or more fluid chambers are used. Some of the fluid chambers may hold fluid which is used for producing lysate from the sample. Other chambers may hold fluids such as washing fluids and amplification solution. The reaction chambers are used to perform the different steps of the detection such as washing, lysis, and amplification.

In preferred embodiments describing the present invention, all reagents required for performing an assay are pre-positioned within the microfluidic device so that the device is a self-contained disposable apparatus for performing nucleic acid assays. Suitable means include biochips based on a DNA microarray or protein microarray, and/or devices for conducting thermo cycling (e.g. PCR, LCR, and others) and/or means for sequencing. Preferably, the microfluidic system will incorporate means for performing thermo cycling, preferably polymerase chain reaction (PCR) or reverse transcription polymerase chain reaction (RT-PCR). PCR methods are well known in the art and rely on thermal cycling, consisting of cycles of repeated heating and cooling of the reaction for nucleic acid melting and enzymatic replication of the nucleic acid. Such amplification reactions typically employ target nucleic acid and reaction components such as a heat-stable DNA polymerase (for instance Taq polymerase), nucleotides and oligonucleotides (for instance primers, probes, blockers, . . . ) required for initiation of nucleic acid synthesis. In preferred applications, the microsystem will apply thermo cycling using reagents in dried-down form present in the microfluidic device. The sample will be treated as described in the present invention to form a lysate and reagents pre-positioned in the microfluidic device are reconstituted at the point of testing by the lysate. Accordingly, the lysate allows for downstream nucleic acid analysis directly in the lysate. Typically, micro pneumatic controllers are used to direct the lysate and the reagents as required for completing the assay. Assays may include end-point or real time detection, both methods are well known in the art.

PCR related terminology as used in the example section:

"Cq" refers to quantification cycle, the fractional cycle number where fluorescence increases above the threshold. Also referred to as Ct (threshold cycle).

"Threshold" refers to the arbitrary level of fluorescence used for Cq determination and should be set above the baseline and within the exponential growth phase of the amplification plot.

"Baseline" refers to the initial cycles of PCR where there is little to no change in fluorescence.

"Amplification plot" refers to a plot of fluorescent signal versus cycle number.

"RFU or relative fluorescence unit" is a unit of measurement used in analysis which employs fluorescence detection.

It is also an aspect of the present invention to provide for compositions for releasing nucleic acid from a biological sample enabling direct nucleic acid analysis in a microfluidic system, which compositions comprise a surfactant compatible with downstream nucleic acid analysis systems. Preferably, the composition when contacted with a sample will provide a lysate, which lysate in its undiluted form allows for downstream nucleic acid analysis directly in the lysate, and which lysate is compatible with downstream nucleic acid analysis systems. Importantly, the lysate should be directly transportable through a microfluidic system. In certain embodiments, the composition has emulsifying activity and includes at least a surfactant, preferably a non-ionic surfactant. Preferably, the lysate is in an undiluted form or in a minor diluted form.

An "emulsion" is a mixture of two or more liquids that are normally immiscible (nonmixable or unblendable). An emulsifier (also known as an "emulgent") is a substance that stabilizes an emulsion by increasing its kinetic stability. One class of emulsifiers is known as "surface active substances", or surfactants.

"Surfactant" as used herein, refers to a compound that lowers the surface tension of a liquid, the interfacial tension between two liquids, or that between a liquid and a solid. These surface-active agents generally comprise a hydrophobic portion and a hydrophilic portion. Surfactants may amongst others act as emulsifiers. Surfactants may be categorized as anionic, nonionic, zwitterionic, or cationic, depending on whether they comprise one or more charged groups.

Nonionic surfactants contain non-charged polar groups and have no charge. Examples of non-ionic surfactants are: BigCHAP (i.e. N,N-bis[3-(D-gluconamido)propyl]cholamide); bis(polyethylene glycol bispmidazoyl carbonyl]); polyoxyethylene alcohols, such as Brij® 30 (polyoxyethylene(4) lauryl ether), Brij® 35 (polyoxyethylene(23) lauryl ether), Brij® 35P, Brij® 52 (polyoxyethylene 2 cetyl ether), Brij® 56 (polyoxyethylene 10 cetyl ether), Brij® 58 (polyoxyethylene 20 cetyl ether), Brij® 72 (polyoxyethylene 2 stearyl ether), Brij® 76 (polyoxyethylene 10 stearyl ether), Brij® 78 (polyoxyethylene 20 stearyl ether), Brij® 78P, Brij® 92 (polyoxyethylene 2 oleyl ether); Brij® 92V (polyoxyethylene 2 oleyl ether), Brij® 96V, Brij® 97 (polyoxyethylene 10 oleyl ether), Brij® 98 (polyoxyethylene(20) oleyl ether), Brij® 58P, and Brij® 700 (polyoxyethylene(IOO) stearyl ether); Cremophor® EL (i.e. polyoxyethylenglycerolthhcinoleat 35; polyoxyl 35 castor oil); decaethylene glycol monododecyl ether; decaethylene glycol mono hexadecyl ether; decaethylene glycol mono tridecyl ether; N-decanoyl-N-methylglucamine; n-decyl [alpha]-D-glucopyranoside; decyl [beta]-D-maltopyranoside; digitonin; n-dodecanoyl-N-methylglucamide; n-dodecyl [alpha]-D-maltoside; n-dodecyl [beta]-D-maltoside; heptaethylene glycol monodecyl ether; heptaethylene glycol monododecyl ether; heptaethylene glycol monotetradecyl ether; n-hexadecyl [beta]-D-maltoside; hexaethylene glycol monododecyl ether; hexaethylene glycol monohexadecyl ether; hexaethylene glycol monooctadecyl ether; hexaethylene glycol monotetradecyl ether; Igepal® CA-630 (i.e. nonylphenyl-polyethylenglykol, (octylphenoxy)polyethoxyethanol, octylphenyl-polyethylene glycol); methyl-6-O—(N-heptylcarbamoyl)-[alpha]-D-glucopyranoside; nonaethylene glycol monododecyl ether; N-nonanoyl-N-methylglucamine; octaethylene glycol monodecyl ether; octaethylene glycol monododecyl ether; octaethylene glycol monohexadecyl ether; octaethylene glycol monooctadecyl ether; octaethylene glycol monotetradecyl ether; octyl-[beta]-D-glucopyranoside; pentaethylene glycol monodecyl ether; pentaethylene glycol monododecyl ether; pentaethylene glycol monohexadecyl ether; pentaethylene glycol monohexyl ether; pentaethylene glycol monooctadecyl ether; pentaethylene glycol monooctyl ether; polyethylene glycol diglycidyl ether; polyethylene glycol ether W-1; polyoxyethylene 10 tridecyl ether; polyoxyethylene 100 stearate; polyoxyethylene 20 isohexadecyl ether; polyoxyethylene 20 oleyl ether; polyoxyethylene 40 stearate; polyoxyethylene 50 stearate; polyoxyethylene 8 stearate; polyoxyethylene bis (imidazolyl carbonyl); polyoxyethylene 25 propylene glycol stearate; saponin from quillaja bark; sorbitan fatty acid esters, such as Span® 20 (sorbitan monolaurate), Span® 40 (sorbitane monopalmitate), Span® 60 (sorbitane monostearate), Span® 65 (sorbitane tristearate), Span® 80 (sorbitane monooleate), and Span® 85 (sorbitane trioleate); various alkyl ethers of polyethylene glycols, such as Tergitol® Type 15-S-12, Tergitol® Type 15-S-30, Tergitol® Type 15-S-5, Tergitol® Type 15-S-7, Tergitol® Type 15-S-9, Tergitol® Type NP-10 (nonylphenol ethoxylate), Tergitol® Type NP-4, Tergitol® Type NP-40, Tergitol® Type NP-7, Tergitol® Type NP-9 (nonylphenol polyethylene glycol ether), Tergitol® MIN FOAM 1×, Tergitol® MIN FOAM 2×, Tergitol® Type TMN-10 (polyethylene glycol thmethylnonyl ether), Tergitol® Type TMN-6 (polyethylene glycol thmethylnonyl ether), Triton® 770, Triton® CF-10 (benzyl-polyethylene glycol tert-octylphenyl ether), Triton® CF-21, Triton® CF-32, Triton® DF-12, Triton® DF-16, Triton® GR-5M, Triton® N-42, Triton® N-57, Triton® N-60, Triton® N-101 (i.e. polyethylene glycol nonylphenyl ether;

polyoxyethylene branched nonylphenyl ether), Triton® QS-15, Triton® QS-44, Triton® RW-75 (i.e. polyethylene glycol 260 mono(hexadecyl/octadecyl) ether and 1-octadecanol), Triton® S P-135, Triton® SP-190, Triton® W-30, Triton® X-15, Triton® X-45 (i.e. polyethylene glycol 4-tert-octylphenyl ether; 4-(1,1,3,3-tetramethylbutyl)phenyl-polyethylene glycol), Triton® X-100 (t-octylphenoxypolyethoxyethanol; polyethylene glycol tert-octylphenyl ether; 4-(1,1,3,3-tetramethylbutyl)phenyl-polyethylene glycol), Triton® X-102, Triton® X-1 14 (polyethylene glycol tert-octylphenyl ether; (1,1,3,3-tetramethylbutyl)phenyl-polyethylene glycol), Triton® X-165, Triton® X-305, Triton® X-405 (i.e. polyoxyethylene(40) isooctylcyclohexyl ether; polyethylene glycol tert-octylphenyl ether), Triton® X-705-70, Triton® X-151, Triton® X-200, Triton® X-207, Triton® X-301, Triton® XL-80N, and Triton® XQS-20; tetradecyl-[beta]-D-maltoside; tetraethylene glycol monodecyl ether; tetraethylene glycol monododecyl ether; tetraethylene glycol monotetradecyl ether; triethylene glycol monodecyl ether; thethylene glycol monododecyl ether; triethylene glycol monohexadecyl ether; triethylene glycol monooctyl ether; triethylene glycol monotetradecyl ether; polyoxyethylene sorbitan fatty acid esters, such as TWEEN® 20 (polyethylene glycol sorbitan monolaurate), TWEEN® 20 (polyoxyethylene (20) sorbitan monolaurate), TWEEN® 21 (polyoxyethylene (4) sorbitan monolaurate), TWEEN® 40 (polyoxyethylene (20) sorbitan monopalmitate), TWEEN® 60 (polyethylene glycol sorbitan monostearate; polyoxyethylene (20) sorbitan monostearate), TWEEN® 61 (polyoxyethylene (4) sorbitan monostearate), TWEEN® 65 (polyoxyethylene (20) sorbitanthstearate), TWEEN® 80 (polyethylene glycol sorbitan monooleate; polyoxyethylene (20) sorbitan monooleate), TWEEN® 81 (polyoxyethylene (5) sorbitan monooleate), and TWEEN® 85 (polyoxyethylene (20) sorbitan trioleate); tyloxapol; n-undecyl [beta]-D-glucopyranoside, MEGA-8 (octanoyl-N-methylglucamide); MEGA-9 (nonanoyl-N-methylglucamide); MEGA-10 (decanoyl-N-methylglucamide); methyl heptylcarbamoyl glucopyranoside; octyl-glucopyranoside; octyl-thioglucopyranoside; octyl-[beta]-thioglucopyranoside; and various combinations thereof.

As shown in the example section, sample treatment with a composition comprising a non-ionic surfactant such as polyglycol ethers having the formula of R—O—(CH2CH2O)n H wherein the number of ethylene oxides is over 7 (n>7), leads to thermocycling-ready lysates without requiring a separate nucleic acid isolation step.

In preferred embodiments the non-ionic surfactant is an Cx fatty alcohol PEG ether has the formula R—O—$(CH_2CH_2O)_nH$ wherein n>7; n≥8; or n=8; and/or R comprises 12≤C≤38; preferably R comprises C13; preferably R comprises C38; most preferably R is $CH_3(CH_2)_7$—CH=CH—$(CH_2)_8$ (oleyl or cis-9-octadecenyl); or most preferably R is $(CH_2)_{11}(CH_3)_2$.

Thus, in certain embodiments, n is 7, 8, 9, 10, 11, 12 or more; and/or R comprises C12, C13, C14, C15, C16, C17, C18, C19, C20, C21, C23, C24, C25, C26, C27, C28, C29, C30, C31, C32, C33, C34, C35, C36, C37, C38. The non-ionic surfactant may be linear or have a branched structure. The non-ionic surfactant may be in liquid form or solid at ambient temperature.

In preferred embodiments the non-ionic surfactant is a C13 fatty alcohol PEG ether; an iso-tridecyl fatty alcohol PEG ether; or an oleyl fatty alcohol PEG ether having 8 ethylene oxide residues Most preferably the non-ionic surfactant is Genapol® X-080 wherein R is $(CH_2)_{11}(CH_3)_2$ and n is 8.

Most preferably the non-ionic surfactant is Oleth®-8 and R is $CH_3(CH_2)_7$—CH=CH—$(CH_2)_8$ and n is 8.

Genapol® X-080 is a chemical product commercialized by Sigma-Aldrich® and its Chemical Abstract Service number (CAS number) is 9043-30-5. Oleth®-8 corresponds to (Z)-3,6,9,12,15,18,21,24-Octaoxadotetracont-33-en-1-ol (CAS number 27040-03-5).

As shown in the example section, the liquefaction composition comprises Oleth®-8. The non-ionic surfactant is present between about 0.10 to about 0.40%, between about 0.15 to about 0.35%, between about 0.20 to about 0.30%, about 0.25%, or 0.25%. Because stock solutions of Oleth®-8 are usually made in DMSO (50% w/v), one of the preferred compositions in addition contains DMSO. DMSO is thus present in an amount relative to the amount of Oleth®-8 present in the composition. In case the non-ionic surfactant is present in about 0.35%, or 0.25%, then DMSO is present in about 0.35%, or 0.25%.

Conventional liquefaction methods incorporate organic solvents in their liquefaction composition or use organic solvents for allowing such downstream applications. As mentioned already, this is particularly true in methods for isolating components such as nucleic acids from wax-embedded samples (e.g. xylene for dissolving paraffin). The methods of the present invention has the advantage that no organic solvents are required and current methods incorporating the non-ionic surfactant permit automated removal of embedded wax and liberation of the components without use of organic solvents. This is particularly beneficial because it puts the liberated nucleic acids in a condition and environment that interfaces with downscale applications requiring enzymatic activity such as downscale amplification processing. Thus, in certain embodiments, the liquefaction composition contains no organic solvents. In preferred embodiments, submerging a wax-embedded slice in a liquefaction buffer performs liquefaction. Typically, the total sample area is inclusive paraffin and varies between about 20 cm2 to about 1 mm2. A 20 cm2 total sample area may for instance result in 5 slices of 4 cm2 Typically, the amount of wax-embedded slice varies between about 50 µm to about 3 µm, between about 40 µm to about 3 µm, between about 30 µm to about 3 µm, between about 20 µm to about 3 µm, between about 15 µm to about 5 µm, between about 13 µm to about 5 µm, between about 12 µm to about 5 µm, between about 11 µm to about 5 µm, about 10 µm to about 5 µm, 10 µm, 9 µm, 8 µm, 7 µm, 6 µm, or 5 µm. Typically, a slice is liquefied in a liquefaction composition volume ranging from about 10 ml to about 50 µL, from about 5 ml to about 250 µL, about 1 ml to about 500 µL. Preferably, the slice is liquefied in about 1 ml, 900 µL, 800 µL, 700 µL or 600 µL of the liquefaction composition. More preferably, the slice is liquefied in about 1 ml, 900 µL, 800 µL, 700 µL, 600 µL, 500 µL, 400 µL, 300 µL or 200 µL of the liquefaction composition.

In certain embodiments, the composition further contains a proteolytic enzyme. Proteases are also known as proteinases are proteolytic enzymes and are involved in digesting proteins. In preferred embodiments, the protease is a heat stable protease that can be heated to moderate temperatures without losing efficacy such as proteinase K. Other examples of heat stable proteases, engineered or naturally occurring are well known in the art. The concentration of the protease in the composition is between about 0.1 µg/ml to about 5000 µg/ml, between about 1 µg/ml to about 4000 µg/ml, between about 10 µg/ml to about 3000 µg/ml, between about 100

µg/ml to about 2000 µg/ml. Preferably it is between about 500 µg/ml to about 1500 µg/ml, between about 600 µg/ml to about 1400 µg/ml, between about 800 µg/ml to about 1200 µg/ml, between about 900 µg/ml to about 1100 µg/ml, between about 950 µg/ml to about 1050 µg/ml or is about 0.1, 1, 2, 3, 4, 5, 10, 15, 20, 30, 50, 75, 100, 125, 150, 200, 300, 400, 500, 600, 700, 800, 900, 1000, 1100, 1200, 1500 µg/ml or any range therein. In a preferred embodiment, the concentration of the protease in the composition is about 1000 µg/ml, or 1000 µg/ml. Amplification of the nucleic acid is performed after inactivation of the protease. Thus, direct nucleic acid analysis may include a protease inactivation step.

One way to improve testing results is to increase the signal obtained from a given sample. Increased signal can amongst others be obtained by increasing the accessibility of the target. Implementation of certain conditions such as for instance temperature heating, HIFU, exposure time, mixing and buffering may improve quality of the emulsified lysate and liberation of the target molecules.

In certain embodiments, the liquefaction composition for liberating nucleic acids from a sample requires heating. In particular embodiments, conditions suitable for generating an emulsified lysate require incubating the liquefaction composition at a temperature suitable for releasing nucleic acid from the biological sample. Factors influencing the solubilisation time include temperature, thickness of the specimen section and wax composition. Incubation in the methods of the present invention is for a time and temperature suitable to release the desired nucleic acid from the sample in an amount and concentration adequate for the intended analysis. In certain embodiments, the incubation is carried out at a temperature that varies from room temperature (20° C.) to a higher temperature. In certain embodiments, the incubation is carried out at a temperature ranging from about 35° C. to about 99° C., from about 45° C. to about 95° C., from about 52° C. to about 90° C., from about 60° C. to about 80° C., from about 55° C. to about 65° C. Preferably, the incubation is at a temperature of 55° C., 56° C., 57° C., 58° C., 59° C., 60° C., 61° C., 62° C., 63° C., 64° C. or 65° C. Initial temperature can be followed by a higher temperature for inactivating enzyme (e.g. proteolytic enzyme) function present in the composition. Typical inactivating temperatures vary from about 90° C. to about 99° C., from about 92° C. to about 97° C. Preferably, the inactivating temperature is about 95° C.

Typically the wax-embedded specimen is contacted with the liquefaction composition of the invention for a time sufficient to solubilize all or part of the wax embedded specimen. Good results were obtained with incubation times varying from about 2 min to about 20 min. For the examples described, liquefaction was performed by submerging one 10 µm FFPE slice in 1 ml liquefaction composition, followed by heating for 20 min at 60° C. and 10 min at 95° C. As shown in the example section, the DNA released in the emulsified lysate was suitable for direct microfluidic analysis without requiring xylene or ethanol extractions of the paraffin and/or nucleic acids.

Conventional methods for mixing and heating the sample and the liquefaction composition are well known in the art. For smaller volume applications and processing in microfabricated analysers it may be beneficial to apply High-Intensity Focused Ultrasound (HIFU, or sometimes also abbreviated as FUS) for heating and micro cavitation of the samples. In certain embodiments, HIFU is applied for heating or after a heating step. In preferred embodiments, the HIFU power ranges from about 2 Watt to about 15 Watt, from about 6 Watt to about 9 Watt. Preferably, the HIFU power is between 2 Watt to 10 Watt, or any range therein. Most preferably, the HIFU power is 4 Watt, or any lower value thereof. Preferably, the HIFU power is 2, 2.25, 2.5, 2.75, 3, 3.25, 3.5, 3.75 or 4 Watt and is applied for 5 to 20 minutes.

In certain embodiments, the composition has buffering capacities that range between about pH6 to about pH10, between about pH7 to about pH9. Typically, the composition of the present invention comprises 10 mM Tris pH8.

Sample treatment with the composition in the methods of the invention will result in a lysate.

It is a requirement in some of the embodiments of the present invention that the lysate, whether or not emulsified lysate, comprising the non-ionic surfactant is compatible with downstream nucleic acid analysis. Consequently, further processing may require adequate dilution of compositions (e.g. liquefaction composition, emulsified lysate) containing the non-ionic surfactant. Adequate dilution factors range from about 5 times to about 2 times, 4 times to about 4 times to about 2 times, or any range therein. Preferably, the composition is diluted about 3 times. In a preferred embodiment, the lysate resulting from the contacting of the composition with the sample is used in an undiluted form for further downstream processing and nucleic acid analysis. In a further preferred embodiment, the composition is diluted about 2 times.

The most common cause of amplification failure is amplification inhibition, wherein one or more undesirable components of a sample being tested are not sufficiently eliminated during nucleic acid purification. Melanin contained in pigment cells in a variety of tissues co-purifies with nucleic acid in standard DNA and RNA procedures and its presence has an inhibitory effect on PCR, RT-PCR or other downstream nucleic acid analysis methods. This problem can be circumvented by separating melanin from the nucleic acid by for instance column chromatography, filtering, nucleic acid precipitation, addition of BSA, or by using a polymerase that is less susceptible to an inhibitor. As shown in the example section of the present invention, the problem is solved by providing adequate liquefaction compositions which contain a non-ionic surfactant that prevents inhibition of amplification by melanin. Thus, in certain embodiments, the liquefaction composition requires a non-ionic surfactant that prevents inhibition of amplification by melanin. The non-ionic surfactant may further prevent inhibition of amplification by inhibitors such as, but not limited to, hemoblobin, heme, myoglobin, immunoglobin, lactoferrin, tar, or collagen for instance.

Thus, the lysate can be processed directly for nucleic acid analysis without requiring purification of the released nucleic acids present in the lysate. However, although not necessarily required, parts or all of the lysate may be subjected to a procedure for nucleic acid extraction or isolation. This may appear advantageous in certain assay set ups. Methods applicable for nucleic acid extraction are well known in the art.

It is to be understood that both the foregoing general description and detailed description are exemplary and explanatory only and are not restrictive of the invention, as claimed. In this application the use of singular includes the plural unless specifically stated otherwise. In this application the use of "or" means "and/or" unless stated otherwise. The use of the terms "including", "includes" or "included" is not limiting.

The section headings are for organizational purposes only and are not to be construed as limiting the subject matter described. All documents cited in this application, including patents, patent applications, articles and books are expressly incorporated by reference in their entirety of any purpose.

EXAMPLES

Example 1. Liquefaction Method for Nucleic Acid Release from FFPE Samples

Human FFPE samples were contacted with a liquefaction composition to provide an emulsified lysate in which nucleic acid is released. The composition contains additives allowing emulsification of the paraffin such that digestion of the tissue sample occurs in the presence of paraffin. The composition is a liquefaction buffer comprising a non-ionic detergent. The liquefaction composition consists of 10 mM Tris pH 8, 0.25% Oleth®-8, and 1 mg/ml proteinase K. Because stock solutions of Oleth®-8 are made in DMSO (50% w/v), the composition in addition contains 0.25% DMSO. Good liquefaction results were obtained with applied heating conditions varying between 55° C. and 65° C. and incubation times varying between 2 min and 20 min. For the examples described, liquefaction was performed by submerging one 10 μm FFPE slice in 1 ml liquefaction composition, followed by heating for 20 min at 60° C. and 10 min at 95° C. As shown in the further examples, the DNA released in the emulsified lysate was suitable for direct microfluidic analysis without requiring xylene or ethanol extractions of the paraffin.

Example 2. DNA Yield Comparison Between Liquefaction and Column-Based Extraction DNA yields of 10 μm FFPE slices obtained by a column-based extraction method and the described liquefaction procedure were compared. Column-based DNA extraction was performed using the Qiagen QIAamp DNA FFPE Tissue Kit according to the manufacturer's instructions. After elution, the volume of extracted DNA was adjusted to 1 ml to allow comparison with liquefied DNA. DNA concentration was measured using the Qubit dsDNA BR assay kit on the Qubit fluorometer 2.0 according to the manufacturer's instructions. Delta Cq (Liq–Extr) represents the difference in Cq between liquefied and column-extracted DNA; Cq values were obtained by performing a TaqMan®-based qPCR reaction for the wildtype BRAF gene based on Hamfjord et al (Diagn Mol Pathol 2011; 20:158-165). The results are shown in Table 1.

TABLE 1

DNA yields and Δ Cq (Liq − Extr)

| Sample ID | DNA yield from liquefaction of 1 FFPE slice (ng) | DNA yield from extraction of 1 FFPE slice (ng) | Δ Cq (Liq − Extr) |
|---|---|---|---|
| Sample 1 | 4548 | 1069 | 2.4 |
| Sample 2 | 824 | 77 | −1.0 |
| Sample 3 | 6620 | 852 | 3.3 |
| Sample 4 | 2788 | 877 | 1.4 |
| Sample 5 | 2416 | 555 | 2.4 |
| Sample 6 | 5140 | 542 | 2.6 |
| Sample 7 | 1756 | 885 | 1.6 |
| Sample 8 | 1020 | 125 | 2.2 |
| Sample 9 | 1160 | 65 | 1.8 |
| Sample 10 | 3640 | 1300 | 0.8 |
| Sample 11 | 1168 | 45 | 3.6 |
| Sample 12 | 3336 | 508 | 1.3 |
| Sample 13 | 12788 | 442 | 1.0 |
| Sample 14 | 2144 | 1051 | 1.0 |
| Sample 15 | 460 | 75 | 2.1 |
| Sample 16 | 2212 | 1013 | 1.8 |
| Sample 17 | 2664 | 1481 | 1.1 |
| Sample 18 | 23120 | 95 | 4.0 |
| Sample 19 | 1848 | 789 | 1.4 |
| Sample 20 | 14160 | 190 | 4.1 |
| Sample 21 | 5224 | 409 | 3.2 |
| Sample 22 | 3796 | 388 | 2.0 |
| Sample 23 | 2936 | 696 | 1.9 |

As shown in Table 1, for all samples DNA yields were higher with the liquefaction method, except for sample 2 where the DNA yield following the extraction method was higher when compared to the DNA yield following present liquefaction method. Also, as shown in the rightmost column of table 1, the difference in Cq value between DNA obtained by liquefaction and column-based extraction indicates that more copies of target DNA can be amplified in the liquefaction condition. In agreement with the DNA quantification results, only sample 2 showed a negative ΔCq value, corresponding to less amplifiable DNA in this liquefied slice.

Example 3. qPCR Functionality of DNA Using Commercial Liquefaction Methods qPCR functionality of DNA liberated in present emulsified lysate and in a commercial available liquefaction composition, QuickExtract™ FFPE DNA Extraction Solution (Epicentre, Madison, Wis.) was compared. Liquefaction of 10 μm FFPE slices and subsequent qPCR analysis were performed as described in the previous example. The volume of the commercial liquefaction composition (Epicentre QuickExtract™ FFPE DNA Extraction Solution) was adjusted to allow 1:1 comparison with the present liquefaction composition. The resulting liquefied lysate was used as input material for qPCR; reactions were performed in a 25 μl reaction volume using a TaqMan®-based detection reaction for the wildtype BRAF gene based on Hamfjord et al (Diagn Mol Pathol 2011; 20:158-165)

FIG. 1 visualizes amplification results on DNA liberated from an FFPE sample in the emulsified lysate containing the detergent Oleth®-8 (grey) and on DNA liberated from the FFPE sample in the commercial liquefaction composition (black). Cross-marked curves represent amplification on almost undiluted emulsified lysate samples (20 μL/5 μL, template/PCR mix), circle-marked curves represent amplification on 4-fold diluted emulsified lysate samples. Under the 80% template condition, the commercial liquefaction composition completely inhibits PCR, and therefore further 4-fold dilution was required to allow qPCR analysis. In contrast, the present liquefaction composition containing the detergent Oleth®-8 is compatible with direct downstream PCR analysis, allowing more template DNA (higher copy number) to be used in the PCR and thereby improving the sensitivity of the PCR analysis.

Example 4. Functionality of Liquefaction Compositions in a Microfluidic System

Functionality of the several liquefaction compositions in microfluidic system processing was explored.

Liquefaction of 3 different FFPE samples was performed using 4 different buffers (with/without detergent and with/without proteinase K), using single consecutive 10 μm FFPE slices for each condition. Liquefaction and PCR processing of the sample was performed in a microfluidic system as described in EP1896180, EP1904234 and EP2419705. Samples were liquefied in 1 ml of the liquefaction composition and heated using the aforementioned conditions. The resulting liquefied mixture was used undiluted as input material for qPCR using the aforementioned amplification conditions. Amplifiable DNA was assessed via qPCR for the wildtype BRAF gene on the liquefied mixture tested.

Table 2 summarizes the ΔCq values obtained for the compositions containing the detergent relative to the reference compositions omitting the detergent. In the context of a microfuidic path in the microfluidic cartridge, adding a detergent like Oleth®-8 to the liquefaction composition lowers the Cq value with an average of 3.8, indicating improved liberation of DNA compared to the reference composition without detergent. Adding proteinase K further improves the Cq value with an average of 1.5. Thus, there is an improvement in release of DNA from the 3 FFPE samples by adding a detergent to the liquefaction composition.

TABLE 2

| ΔCq (Avg ± stdev) | Composition |
| --- | --- |
| reference | Tris |
| 3.8 ± 1.4 | Tris + Oleth ®-8 |
| reference | Tris + protK |
| 5.3 ± 4.1 | Tris + protK + Oleth ®-8 |

Figure 2:
FIG. 2: Picture demonstrating incompatibility of the commercial buffer with the microfluidic qPCR system. Circle marks formation of air bubbles in the PCR chamber following pumping of the commercial buffer through the microfluidic path.

The functionality of a commercially available liquefaction buffer QuickExtract™ FFPE DNA Extraction Solution (Epicentre, Madison, Wis.) in the microfluidic system was also tested. Pumping the commercial liquefaction buffer through the microfluidic path of the microfluidic cartridge to the 5 PCR chambers reproducibly resulted in the formation of air bubbles (FIG. 2, circled PCR chamber). Such air bubbles should be avoided because they impair qPCR analysis after filling of the PCR chamber. In contrast, no air bubbles were observed when the liquefaction buffer containing Oleth®-8 was transferred to the PCR chamber, indicating that the physico-chemical properties of Oleth®-8 are compatible with the microfluidics of the cartridge.

Figure 3:
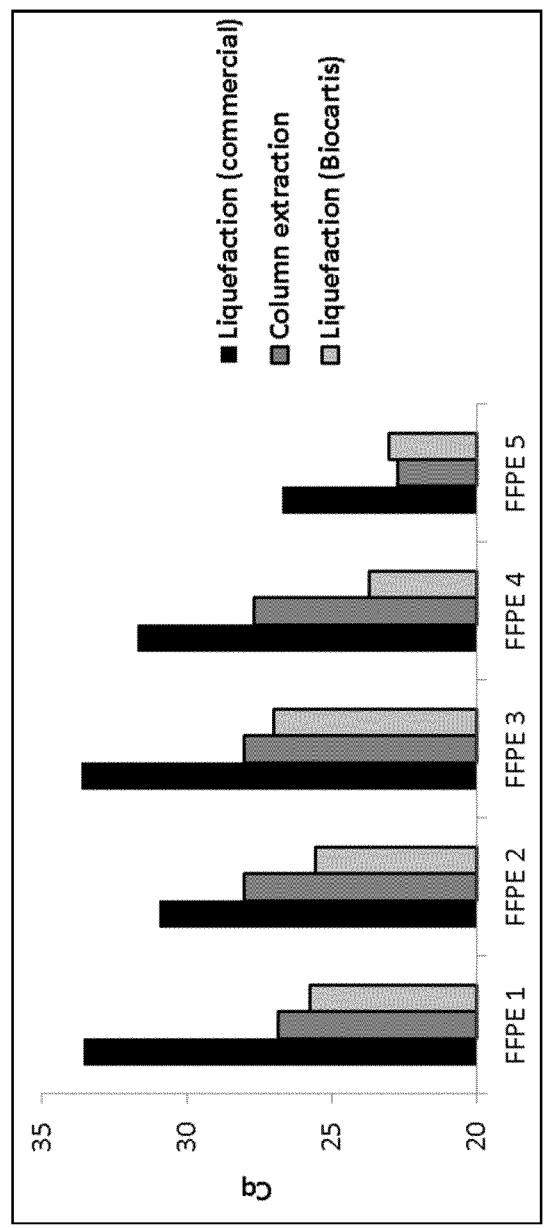
FIG. 3: Cq graph demonstrating a performing assay practised on DNA from FFPE melanoma samples with varying amounts of melanin, following different DNA extraction/liquefaction methods. X-axis represents FFPE samples; Y-axis represents Cq values obtained; bars represent: DNA liquefaction using a commercial solution (Black), Column-based DNA extraction (Dark grey), and DNA liquefaction from present invention (Light grey). Lower values indicate a lower qPCR threshold value and hence improved sensitivity for DNA analysis.

Example 5. Functionality of Liquefaction Compositions in the Presence of PCR Inhibitors The performance on samples containing variable amounts of the well-known PCR inhibitor melanin following DNA extraction or liquefaction was compared. 1 FFPE slice per sample was either i) liquefied in 800 μL of the liquefaction composition containing Oleth®-8 or ii) liquefied in the commercial liquefaction composition (Epicentre QuickExtract™ FFPE DNA Extraction Solution) or iii) processed using the column-based extraction method (Qiagen QIAamp DNA FFPE Tissue kit) according to the manufacturer's instructions and eluted in 200 μL H2O or TE. Liquefactions were performed as previously described and the resulting mixture was used undiluted as input material for PCR. qPCR reactions were performed as described. FIG. 3 indicates the effect of the DNA liberation procedure on qPCR performance of 5 different FFPE samples, containing variable amounts of the well-known PCR inhibitor, melanin. Samples 1-4 contain high amounts melanin (for instance >95% for sample 4), while sample 5 contains no melanin.

Figure 4:
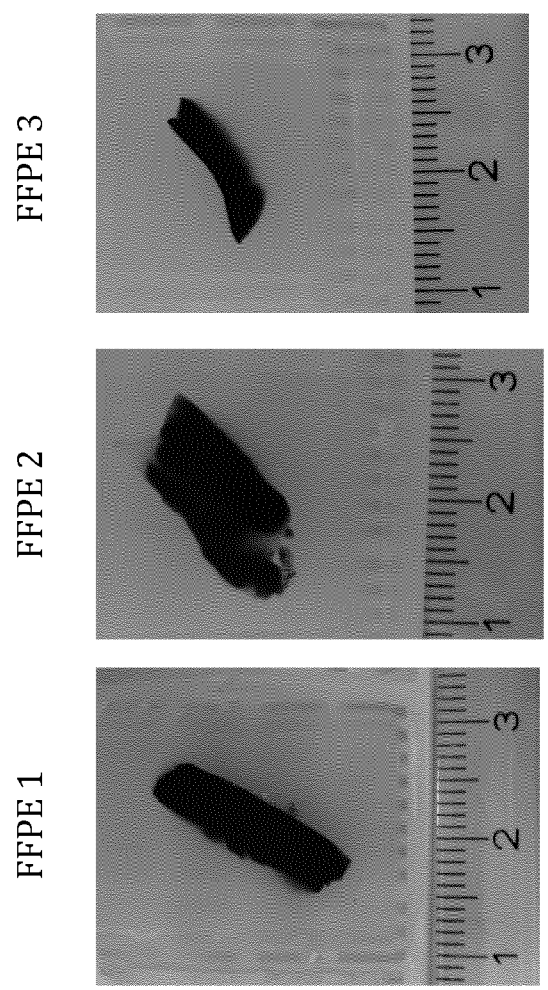
FIG. 4: Visual representation of high melanin containing samples FFPE1, FFPE2 and FFPE3 used in Example 5.
Figure 5:
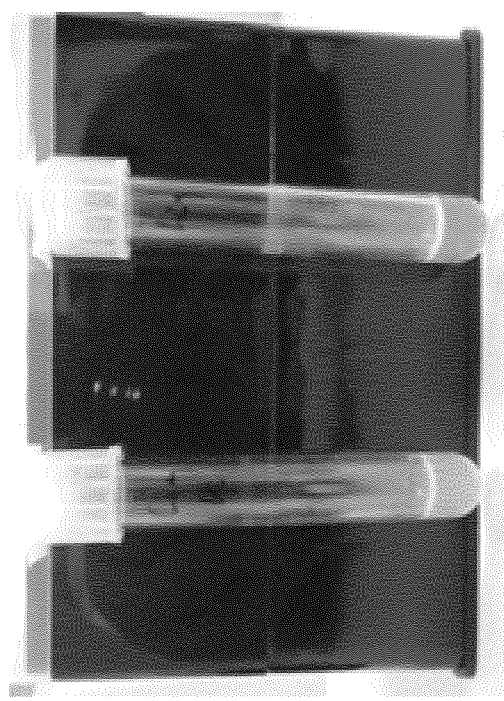
FIG. 5: Picture demonstrating sample liquefaction in combination with a raise in temperature (A) and sample liquefaction in combination with a raise in temperature combined with HIFU treatment (B).
Figure 6A:
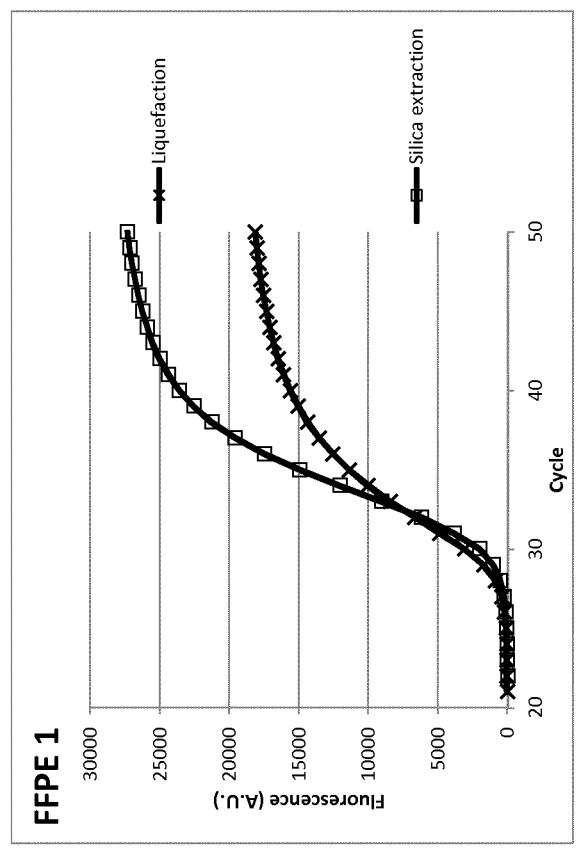
FIGS. 6a and 6b: qRT-PCR curves obtained from liquefied material (X) and silica-extracted RNA (□) from single consecutive 10 μm sections of 2 representative FFPE samples (FFPE 1 and FFPE 2)
Figure 6B:
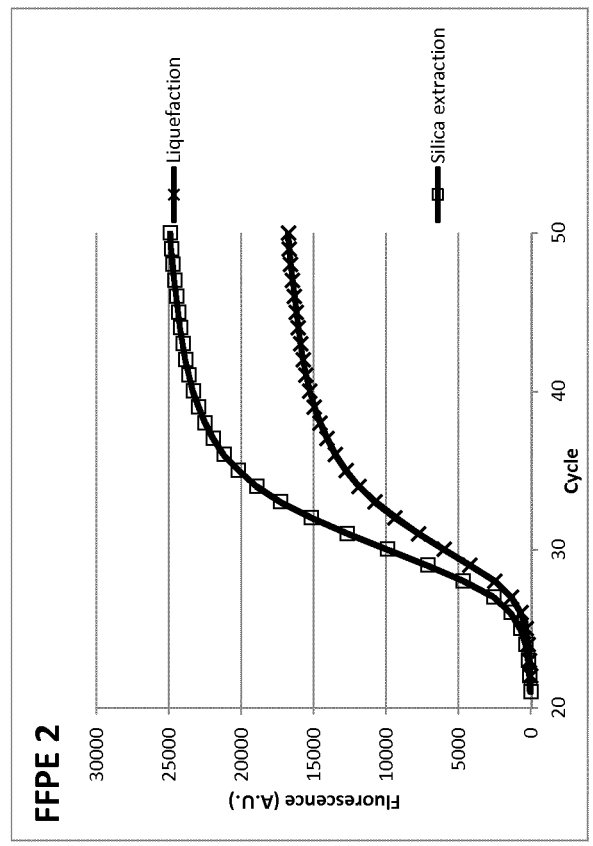

The present liquefaction composition results in superior PCR amplification of DNA compared to the commercial liquefaction composition, regardless of the presence of melanin. The present liquefaction composition generally results in better compatibility with downstream processes compared to column-based DNA extraction for high melanin containing samples. This is for instance evident from the Cq values depicted in FIG. 3 for FFPE 4 following the different methods. A similar performance was observed when no melanin is present. Therefore other realtime PCR inhibitors that are not immediately apparent or known may be present in samples, for which the claimed compositions offer improved performance. FIG. 4 is a visual representation of 3 high melanin-containing samples used in the experiment.

Example 6. Emusifying Capacity of the Liquefaction Buffer with Lysis on the Bench and Lysis in the Lysis Chamber of the Idylla Cartridge For both conditions, one 10 μm slice, cut consecutively from the same FFPE block was submerged in 1 ml of liquefaction buffer. In the bench protocol, the slice was warmed to 60° C. for 15 min in a 1.5 ml tube (Eppendorf) using a heat block (Eppendorf) while shaking (800 rpm). In the cartridge, the temperature was raised stepwise (room temperature, 45° C., 50° C., 54° C. and 58° C.) in 5 about minutes by a combination of peltier (heating) and piezo (high intensity focussed ultrasound or HIFU) functionalization. In the last step, the temperature was raised to 60° C. and maintained for 10 minutes under a HIFU power that never exceeded 2.25 W. After both treatments, 0.5 ml was transferred to a high-optical clarity round bottom tube (5 ml BD falcon), chilled to room temperature and vortexed at maximum power. Although two virtually identical slices were liquefied in the same buffer and volume, a superior paraffin emulsion is obtained by HIFU treatment compared to bench heating and shaking. HIFU treatment reproducibly results in more opaque liquefact and less paraffin deposit (arrow) on the walls of the tube after vortexing.

Example 7. qRT-PCR Curves Obtained from Liquefied Material and Silica-Extracted RNA The figure above shows qRT-PCR curves obtained from liquefied material and silica-extracted RNA from single consecutive 10 μm sections of 2 representative FFPE samples (FFPE 1 and FFPE 2). RNA template material in the liquefaction condition was obtained by processing an FFPE section according to the liquefaction method described above. Briefly, the FFPE section was contacted with the liquefaction composition and heated to 60° C. for 15 min, followed by 95° C. for 10 min in a 1.5 ml tube (Eppendorf) using a heat block (Eppendorf) while shaking (800 rpm). RNA template material in the silica extraction condition was obtained by processing an FFPE section using the Qiagen QIAamp RNA FFPE Tissue Kit according to the manufacturer's instructions. Subsequently, 5 μL template obtained by each method was analyzed in a 25 μL qRT-PCR reaction using a RNA-specific assay for the housekeeping gene B2M.

FIG. 7 demonstrates that a similar threshold cycle ($C_t$) is obtained by using either the liquefaction or silica extraction method for liberating RNA from the FFPE sections.

Accordingly, the RNA released in the emulsified lysate was suitable for direct microfluidic analysis Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

The invention claimed is:

1. A method for releasing nucleic acids contained in a biological sample, the method comprising the step of:
    contacting the biological sample with a composition for converting at least part of the sample into a lysate containing said nucleic acids, said lysate being directly transportable through a microfluidic system,
    wherein the sample is a wax-embedded sample or a formalin fixation and paraffin embedding (FFPE) sample,
    wherein the composition is a liquefaction composition that includes at least a non-ionic surfactant; and
    performing a downstream analysis of a nucleic acid potentially present among the nucleic acids contained in the lysate,
    wherein the downstream analysis
        is performed within the microfluidic system,
        comprises an amplification reaction of the nucleic acid, and
        is a direct analysis of said nucleic acid, comprising providing at least a portion of the lysate containing the nucleic acids into the amplification reaction without purification of the nucleic acids from the non-ionic surfactant included in the liquefaction composition.

2. The method according to claim 1 wherein the amplification reaction comprises thermocycling.

3. The method according to claim 2 wherein the thermocycling comprises PCR.

4. A method according to claim 1 wherein the nucleic acid is DNA or RNA.

5. The method according to claim 1 wherein the non-ionic surfactant has the formula

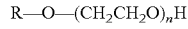

wherein n>7; n≥8; or n=8;
and/or
R comprises 12≤C≤38.

6. The method according to claim 5 wherein R is $CH_3(CH_2)_7$—CH═CH—$(CH_2)_8$ or $(CH_2)_{10}$—CH—$(CH_3)_2$.

7. The method according to claim 5 wherein the non-ionic surfactant is (Z)-3,6,9,12,15,18,21,24-Octaoxadotetracont-33-en-1-ol.

8. A composition for releasing nucleic acid from and for liquefying a wax-embedded or an FFPE biological sample, said composition:
    comprising at least a non-ionic surfactant, wherein the non-ionic surfactant is (Z)-3,6,9,12,15,18,21,24-Octaoxadotetracont-33-en-1-ol or polyethylene glycol monoalkyl ether that has the formula R—O—$(CH_2CH_2O)_n$H wherein n=8; and
    wherein the amount of the non-ionic surfactant is adapted such that when said composition is brought in contact with the biological sample, at least a part of the biological sample is converted into a lysate directly transportable through a microfluidic system, wherein the amount of the non-ionic surfactant in the composition is between 0.10% and 0.40%, said lysate at the same time being suitable for performing a direct analysis of the contained therein released nucleic acid by means of a nucleic acid amplification reaction, wherein said amplification reaction is performed in the presence of said lysate without prior purification of the released nucleic acid from the non-ionic surfactant.

9. A composition for releasing nucleic acid according to claim 8 wherein the non-ionic surfactant is (Z)-3,6,9,12,15,18,21,24-Octaoxadotetracont-33-en-1-ol.

10. A method according to claim 1 wherein the direct analysis comprises providing at least a portion of the lysate into the amplification reaction, wherein the lysate is undiluted or minimally diluted.

11. A method according to claim 3 wherein the PCR comprises real-time detection.

12. A composition for releasing nucleic acid according to claim 8 wherein said lysate is suitable for performing a direct analysis of the released nucleic acid while being undiluted or minimally diluted.

13. A composition for releasing nucleic acid according to claim 8 wherein said lysate is suitable for performing a direct analysis of the released nucleic acid while being diluted 2-fold.

14. The method according to claim 5 wherein the non-ionic surfactant is polyethylene glycol monoalkyl ether.

15. A composition for releasing nucleic acid according to claim 8 wherein the non-ionic surfactant is polyethylene glycol monoalkyl ether.

* * * * *